United States Patent [19]

McGrath et al.

[11] Patent Number: 4,786,590

[45] Date of Patent: Nov. 22, 1988

[54] DIAGNOSTIC AND THERAPEUTIC ASPECTS OF RECEPTOR-MEDIATED LEUKEMOGENESIS

[75] Inventors: Michael S. McGrath, Menlo Park; Irving L. Weissman, Stanford Leroy Hood, Pasadena, all of Calif.

[73] Assignees: California Institute of Technology, Pasadena; The Board of Trustees of the Leland Stanford, Jr. University, Stanford, both of Calif.

[21] Appl. No.: 691,997

[22] Filed: Jan. 15, 1985

[51] Int. Cl.[4] ................ G01N 33/569; G01N 33/574; G01N 33/577; A61K 39/00

[52] U.S. Cl. .......................................... 435/5; 424/86; 435/7; 435/29; 436/519; 436/548; 436/813

[58] Field of Search ................ 436/519, 813, 548; 435/5, 7, 29; 424/85, 86

[56] References Cited

U.S. PATENT DOCUMENTS

| | | | |
|---|---|---|---|
| 4,391,911 | 7/1983 | Tarro | 436/813 X |
| 4,426,446 | 1/1984 | Thompson | 436/813 X |
| 4,513,088 | 4/1985 | Levy | 436/813 X |
| 4,545,738 | 2/1987 | Knowles | 436/813 X |
| 4,599,305 | 7/1986 | Witte | 436/83 X |

OTHER PUBLICATIONS

Weissman, I. L., Life Sciences Research Report, 30, Leukemia, 235-249 (1985).
Cianciolo, G. J. et al., Science, 230 (4724), 453-455 (Oct. 25, 1985).
Cianciolo, G. J. et al., Nature, 311(5986), 515 (Oct. 1984).
Epstein, R. L. et al., Virology, 133(1), 46-55.

*Primary Examiner*—Sidney Marantz
*Attorney, Agent, or Firm*—John P. White

[57] ABSTRACT

Specific binding members are provided for binding to lymphocytic cell surface receptors, which receptors are involved in the activation of a cell from the $G_0$ state into the cell division cycle to proliferate. The cell surface receptors are further characterized by binding to envelope proteins of neoplasia-causing retroviruses, and/or to intact retroviral particles.

12 Claims, No Drawings

DIAGNOSTIC AND THERAPEUTIC ASPECTS OF RECEPTOR-MEDIATED LEUKEMOGENESIS

This work was supported by a Grant CA32031 from the National Cancer Institute, USPHS, CA40041; and VA Merit Review Grant 365/6016.001(016)CP103.

BACKGROUND OF THE INVENTION

1. Field of the Invention

There is a continuing interest and concern with the diagnosis and treatment of neoplastic conditions. A major source of death are neoplastic conditions associated with T- and B-lymphocytes. While much progress has been made in the treatment of lymphoma and leukemia, there are still no generally accepted methods for diagnosis and treating such disease states. It would therefore be of great interest to be able to diagnosis the onset of a lymphocytic neoplastic condition and to treat such condition, whereby the disease could be arrested or eradicated.

2. Description of the Prior Art

Weissman and Baird, Life Sciences Research Report 7 (Koprowski, ed.) p. 135 (1977); McGrath and Weissman, In Normal and Neoplastic Hemapoeitic Cell Differentiation, p. 577. Cold Spring Harbor Press, New York (1978), and Weissman et al., In Life Sciences Research Report, Dahlem Conference, in press, (1984) discuss the receptor-mediated leukemogenesis hypothesis. Hood et al., *Immunology*, 2nd Ed., Benjamin/Cummings Publishing Co. (1984) reports that antigen binding to antigen receptors of immunocompetent lymphocytes starts the chain of events bringing the lymphocytes into the cell cycle. In mice each T-cell lymphoma has specific receptors for the retrovirus which induces it and in mice and in chickens. These receptors are present only on malignant clones which arise late in the pre-leukemic period and are not present on the population of non-malignant cells which proliferate abundantly throughout that period. McGrath et al., *J. Virol.* (1978) 28:819; McGrath and Weissman, *Cell* (1979) 17:65; and McGrath and Weissman, In Human T-cell Leukemia/Lymphoma Virus (Gallo et al., eds.), Cold Spring Harbor Press, New York, p. 205 (1984). Antibodies which prevent virus-binding to lymphoma cells in vitro also prevent their proliferation and this effect is reversible by the addition of free cognate retrovirus for some cell lines. McGrath et al., *Nature* (1980) 285:259. See also McGrath et al., In Experimental Hematology Today (Baum et al., eds.) p. 93 (1982). Allison et al., *J. Immunol.* (1982) 129:2293, report a clonotypic antibody, specific for the T-cell antigen receptor heterodimer on a Radiation Leukemia Virus (RadLV) induced T-cell lymphoma.

SUMMARY OF THE INVENTION

Methods and compositions are provided for diagnosing and treating neoplasias, particularly lymphocytic neoplasia, by employing compositions which bind to, either competitively or non-competitively, cell surface receptors involved with the activation of cells from a resting phase into the cell division cycle to proliferate. The cell surface receptors also bind to an antigenic site of a retrovirus. Particularly, slow transforming retroviral proteins, such as envelope glycoproteins, analogs thereof, or ligands or receptors capable of binding to the surface membrane protein which binds to the retroviral protein and/or to intact retroviral particles, can be employed in a variety of ways to diagnose the presence of neoplastic cells and to treat such cells with various cytostatic or cytotoxic agents.

DESCRIPTION OF THE SPECIFIC EMBODIMENTS

Methods and compositions are provided based on binding sites of transforming retroviruses, particularly slowly transforming viruses, which binding site binds to a cell surface membrane receptor involved in the activation of a cell from the resting phase ($G_0$) into the cell division cycle and proliferation to form clones. By providing molecules which can bind to the cell surface membrane receptor (CSMR) identified by the retroviral protein and/or the intact retroviral particles, host cells susceptible to transformation and the presence of transformed host cells can be diagnosed. Compounds which are capable of binding to such CSMRs and have cytostatic or cytotoxic capability can be used for selective growth inhibition.

Many cell surface membrane proteins are known to be involved with the proliferation of cells as a result of binding to a complementary specific binding member. (By specific binding member is intended a molecule which has a surface conformation where by van der Waal's interactions, dipole interactions, and charge interactions, the conformation selectively binds to another molecule which has a complementary conformation so as to provide for an association constant of at least about $10^5$, preferably at least about $10^7$ liters/mole. Hood et al., *Immunology*, 2nd ed., The Benjamin/Cummings Publishing Co., Inc., Menlo Park, Calif., 1984, p. 58.) By contacting target cells with transforming retroviral proteins or particles and screening for cellular proliferation in vitro or in vivo, the CSMR protein which is complementary to the retroviral protein may be identified. Identification can be achieved in a variety of ways, for example, by lysing the cell and using affinity chromatography, employing the retroviral protein bound to the packing, by Westerns, Ouchterlony double-diffusion, separation of the various proteins followed by titration with the retroviral proteins, or the like. The particular manner in which the cell surface membrane protein is identified is not critical to this invention, the significant factor being that it is characterized by specifically binding to a retroviral protein, particularly an envelope glycoprotein and/or intact retroviral particles, and is involved with the activation of cells from the resting phase to the growth or proliferation phase.

An increasing number of transforming retroviruses, particularly slowly transforming viruses are known, which induce cancers in a wide variety of warm-blooded animals, including mammals and birds, in the absence of an evident oncogene. Illustrative viruses include HTLV-I and -II, feline leukemia virus, murine leukemia virus, avian leukemia virus, mammary tumor viruses, e.g., MMTV, bovine leukemia virus, and the like. While for the most part leukemia viruses are indicated, these are considered to be illustrative of the general class of transforming retroviruses, particularly slowly transforming viruses. Hosts include primates, e.g., humans, domestic animals, birds, etc.

As exemplary of the use of the use of slowly-transforming viruses for identifying specific cell surface membrane proteins, the subject method will be illustrated with leukemogenic iruses as exemplary of the general class of slowly transforming viruses. It is to be understood that the subject methodology has application beyond the lymphocytic cancers.

A large number of cell surface membrane proteins are known to be associated with the activation of cells to enter the cell division cycle. Many of these proteins are cell specific and in the case of B- and T-lymphocytes, the proteins are clonotypic in that the cells have receptors which are specific for a small sub-population of the total population of the type of cell. These receptors, referred to as immunoglobulins in the case of B-cells, and $\alpha, \beta$-heterodimer in the case of T-cells are well-established markers for the B- and T-lymphocytes. Each cell clone may be distinguished by the recognition site of the receptor, which is a variable region specifically related to a complementary binding member.

Other factors associated with activation of cell division for which cell surface receptors exist include the interleukins-1, -2 and -3; epidermal growth factor; $\alpha$ and $\beta$-transforming growth factor; platelet-derived growth factor; etc. In many cases, the various growth factors are cell type specific, being associated with cells of a specific type or organ.

For diagnosing the presence of an enhanced population of the specific CSMR protein, a wide variety of ligands and receptors may be employed. One could use the entire retroviral protein or fragments thereof specific for the CSMR. Alternatively, mimetic analogs may be employed which specifically bind to the CSMR and which may be polypeptides or non-peptide organic molecules. In addition, antibodies may be prepared, either monoclonal or polyclonal, which specifically bind to the region(s) of the CSMR which distinguishes the cell's susceptibility to the binding of the slowly-transforming retrovirus, i.e., the variable region.

For example, in the case of T-cells and B-cells, the cells have specific receptors which include both constant regions and variable regions. The constant regions will be common to all or a substantial proportion of the particular type of cell, while the variable region will be common only to a very small number of the particular type of cell, unless there has been an infection or some other event activating the particular cell or the cell has been transformed to a cancer cell. Therefore, with lymphocytes, one can look to the specific receptors on the surface associated with lymphocyte recognition as part of the immune system. Thus, the presence of a disproportionately high population of a lymphocyte capable of binding to slowly transforming retroviral protein and/or intact retroviral particle would be indicative of oncogenesis.

Monoclonal antibodies are of particular interest for diagnosis and therapy. They can be prepared in conventional ways as described in the literature. See U.S. Pat. Nos. 4,196,265 and 4,271,145 and references cited therein. Whole antibodies or fragments thereof may be employed, such as Fab, F(ab)'$_2$, F$_v$, or the like. Antibodies can be made to the F$_v$ which will mimic the conformation of the CSMR and may act as a competitor for binding to compounds which bind to the CSMR.

By having a compound which specifically binds to the CSMR, one can detect the presence of a tumor by employing a physiological sample and determining the binding of such compound to the cells or, as appropriate, the CSMR in solubilized from in a physiological sample. Physiological samples include blood, serum, plasma, urine, tissue, lymph, or other fluid, solid or semi-solid, where either the cell or the protein may be reasonably suspected of being present.

The compound which binds to the CSMR may be directly or indirectly labeled, so as to be able to detect the presence of the CSMR. By direct labeling is intended covalent bonding to such binding member, while indirect labeling intends labeling of a binding member capable of binding to the compound which binds to the CSMR, but which does not interfere with the binding of such compound to the CSMR.

A wide variety of labels find use, such as radionuclides, enzymes, fluorescers, chemiluminescers, enzyme cofactors, substrates and inhibitors, particles, etc. The patent and technical literature has ample discussion and description of a wide variety of techniques for detecting the presence of a particular analyte, and such discussion need not be elaborated upon here. See, for example, U.S. Patent Nos. 3,817,837 and 4,174,384.

For therapeutic purposes, monoclonal antibodies may be employed which specifically bind to one or more determinant sites of the CSMR, where at least one of the monoclonal antibodies binds to that portion of the CSMR which differentiates the particular CSMR from other CSMR's from other cell types or subsets of such cell types. Where the monoclonal antibody binding is capable of inhibiting proliferation of the cells, the monoclonal antibody may serve as a cytostatic agent in conjunction with other agents for retarding the growth of the particular cell type and killing the particular cell type. Alternatively, the monoclonal antibody may be used to direct other agents to the site of the transformed cells, where such agents may be cytostatic or cytotoxic.

Illustrative agents include radionuclides, e.g., radioactive iodine toxins, particularly the A-chain of toxins, such as ricin and diphtheria toxin, factors involved in complement lysis, or the like. These various techniques have also been extensively described in the literature and do not require exemplification here. See, for example, U.S. Pat. No. 4,340,535 and EPA No. 17,507.

In addition, the subject invention can be used to monitor surgical, chemotherapeutic, or radiotherapeutic removal of cancers by providing for compounds which are complementary to the subject CSMR and specifically bind to such CSMR. By providing for a means for detecting such compounds in the blood stream, one can introduce a known quantity of such compound and determine the rate at which the concentration in the blood stream changes as compared to the rate at which it would change in a normal host. Thus, one can determine whether in fact the cancer cells have been completely removed or are still present and proliferating at the same or a different site from the surgical treatment.

For therapeutic purposes, the complementary members may be administered to the host in a variety of ways, injecting intratumorally, intravenously, intraarterially, subcutaneously, or the like, or administered orally, or other means of administration. The concentration of the subject compounds will vary widely depending upon the nature of the compound, the purpose, the host, and the like. The compound may be administered neat or in a physiologically acceptable carrier, such as water, saline, phosphate buffered saline, alcohol, or the like.

Compositions for diagnosis can be supplied as kits, where a monoclonal antibody specific for the CSMR is provided, which is labeled, or a second labeled antibody is included which binds to the monoclonal antibody. The monoclonal antibody is provided in a formulation which may include buffers, stabilizers, salt, excipients, other proteins, such as albumins to inhibit non-specific binding to surfaces, and the like. Other materials included in the kit would be components necessary for detection, e.g., for an enzyme, enzyme substrates and cofactors. The formulations would be provided as lyophilized powders for reconstitution.

The following examples are offered by way of illustration and not by way of limitation.

EXPERIMENTAL

Monoclonal antibodies were prepared to the polypeptide specified by the variable region of the β-chain of a T-cell receptor found on leukemia cells, variously called Jurkat, J/M or MOLT3. One of these monoclonal antibodies detects not only the cells to which it was raised, but all cells thus far tested which have on their surface receptors which bind the human T-cell leukemia virus HTLV-I. Thus, all leukemia so far tested which bind HTLV-I, whether induced by HTLV-I or not, are detected by this monoclonal antibody.

In the next study, the monoclonal antibody Mab124-40, specific for the T-cell antigen receptor heterodimer on a Radiation Leukemia Virus (RadLV)-induced T-cell lymphoma, C6VL/1 was employed. (Allison et al., supra).

The main assay employed for detecting binding of retroviral protein and/or retroviral particles to cells is as follows. The assay involved measuring the number of cells adhered to a virus-coated plate at the end of the assay by their ability to take up the intracytoplasmic dye, Rose Bengal.

Cells were prepared by 3 washes with serum-free medium and then sedimentation through medium containing 10% FCS (fetal calf serum) at 1 g for 1 hr at 37° C. Cells were then incubated for 2–3 hr at 20° C. at $1 \times 10^6$ cells/ml to shed virus before centrifugation and resuspension to $5 \times 10^6$ cells/ml in medium/5% FCS. Virus was prepared from the supernatant of lymphoma cells grown to confluence in in vitro culture by Amicon filtration concentration and purification by Sepharose 4B chromatography. For use in the plate binding assay, virus was diluted in distilled water and 50μl aliquots were plated into the wells of flexible polyvinyl chloride microtiter plates (Dynatech Laboratories, Alexandria, Va.). Typically 3-fold dilutions from an initial virus concentration of 0.1 or 0.3 OD 260μ/ml were plated. To block non-specific binding of cells, it was necessary to add medium (RPMI 1640) containing FCS for 20 min to each well of the microtiter plate; this was flicked off prior to addition of cells. Cells in 50μl volumes were centrifuged onto the virus-coated plates (1,000 rpm, 30 sec), and then allowed to adsorb for 60 min at 20° C. To measure cell adherence a solution of 0.5% Rose Bengal/0.5% glutaraldehyde in PBS was gently added to the wells of the microtiter plate and left for 1 to 2 min. Dye was then gently drained from the wells and unbound cells washed free with two washes of RPMI 1640 with 5% FCS. Dye was immediately released from bound cells by addition of 150μl 50% ethanol and resuspension with a pipettor. Color in each well was measured spectrophotometrically using a microelisa reader (Dynatech Labs., Alexandria, Va.) with a test wavelength of 540 nm and a reference of 630 nm. Binding to poly-L-lysine-coated wells (50 μgm/ml) was used to measure maximum cell binding and dye uptake (glutaraldehyde was omitted from the dye mix added to these wells). Routine controls were cell binding to uncoated wells since virus-coated plates alone took up no stain. Binding endpoint was taken as the reciprocal of the concentration of virus (OD260 μ/ml) which gave background binding.

Cell Specificity for RadLV/C6VL

The following lymphomas were compared in the described assay for binding to RadLV/C6VL: $1104 \times 5(Ig^-)$ and SC-2L(Ig$^+$) (avian B-cell lymphomas obtained from Mike Bishop); KKT-2 and SL3 (spontaneous AKR T-cell lymphomas obtained from Esther Hays) UNC-1, (a spontaneous B10. A T-cell lymphoma obtained from Geoffrey Haughton); C6VL/1 and BL/VL3, (BL/Ka RadLV-induced T-cell lymphomas obtained from Miriam Lieberman); RAW 112, (an Abelson-virus induced BALB/c pre-B-cell lymphoma obtained from Bill Raschke).

Out of 8 lymphomas compared for binding, 3 out of 5 T-cell lymphomas had very strong avidity for RadLV/C6VL. These were 6CVL/1, BL/VL3 and KK2-2. UNC-1 bound more weakly, and SL3 and the other non-T-cell lymphomas gave almost background binding. However, C6VL/1 cells were shown to have greater specificity for RadLV/C6VL than for heterologous viruses, when free virus was used to inhibit C6VL/1 cell binding to RadLV/C6VL.

Specificity of Free Virus Inhibition

RadLV/C6VL, RadLV/VL3 and SL3LV preparations were compared for their capacity to inhibit the binding of C6VL/1 to RadLV/C6VL. Two fold diluting concentrations of Sepharose 4B column purified virus (from OD260μ/ml=0.25) were incubated with C6VL/1 cells for 60min at 20° C. before addition to the RadLV/C6VL-coated microtiter plate. Data represents the minimum concentration of virus needed to reduce binding to background levels, as measured spectrophotometrically.

The results showed that a 15-fold greater concentration of RadLV/VL3 and SL3LV are needed over RadLV/C6VL to inhibit C6VL/1 binding to plate-bound RadLV/C6VL. The stronger binding observed of cells to plate-immobilized virus than to free virus appears to be the result of multivalent interactions between cells and multiple adjacent virions on the plate.

Antibody inhibition of C6VL/1 binding to RAdLV/C6VL and to the heterologous virus RadLV/VL3 was studied next. C6VL/1 cells and virus-coated microtiter plates for these experiments were prepared as described above. C6VL/1 cells ($5.10^6$/ml in 1.2 ml RPMI/5% FCS) were incubated for 60 min at 4° C. with different concentrations of antibody used over the saturating range. Fifty μl aliquots of cells plus antibody were then added to virus-coated plates, and cell binding measured as described above. The following monoclonal antibodies were used as culture supernatant preparations; Mab124-40, a mouse IgG$_1$, specific for a clonotypic T-cell antigen receptor determinant on C6VL/1 (Allison et al., supra); 30H-12, a rat IgG2b specific for Thy-1.2; B22-249, a mouse IgG2b specific for H-2D$^b$; 8-6.2, a mouse IgG2a specific for Ly-15.2; and 30G-12, a rat IgG2a specific for T200. A rabbit antiserum 8177-R8 prepared against the T-cell antigen receptor heterodimer immunoprecipitated by Mab124-40 was also used. Before use in this assay, antibodies were titrated on C6VL/1 cells using the FACS, and increasing concentrations from minimal saturation were tested for blocking. A colorimetric titration of C6VL/1 binding to diluting concentrations of plate-bound RadLV/C6VL in the presence of 30H-12, or different dilutions of Mab124-40 and 8177-R8 was performed. Average binding endpoints from 3 or 4 experiments were determined for C6VL/1 binding to RadLV/C6VL and RadLV/VL3 in the presence of different antibodies. Standard deviations were ≦0.4 Log OD 260μ/ml for all but 2 data points which were 0.7.

The results demonstrated that the clonotypic antibody Mab124-40 almost completely inhibited the binding of C6VL/1 cells to RadLV/C6VL, but had only minimal effect on the binding to RadLV/VL3. Binding of rhodaminated RadLV/C6VL to C6VL/1 cells was also selectively inhibited by antibody Mab124-40. A rabbit antiserum 8177-r8, McIntyre and Allison, *Cell* (1983) 34:739, raised against constant determinants of the C6VL/1 T-cell antigen receptor heterodimer also inhibited C6VL/1 binding to RadLV/C6VL and more weakly to RadLV/VL3. When other cell surface antibodies were tested with GK1.5 (Ceredig et al., *J. Exp. Med.* (1983) 158:1654) specific for the L3T4 molecule in the T-cell receptor complex, it was found to be weakly inhibitory as was 30H-12 (anti-Thy 1.2). Antibodies specific for other cell surface determinants, namely H-2D$^b$(B22-249), T200(30G-12) and Ly-15.2(A-6.2) were not inhibitory.

Antibodies found to be inhibitory were also tested in an assay involving their adsorption to cells which had been presaturated with RadLV/C6VL viral particles, followed by removal of free antibody by one or two washes with medium before bound antibody was detected in the FACS by a detecting second stage antibody. Mab124-40 was found to be selectively inhibited in binding to C6VL/1 by RadLV/C6VL, but not by RadLV/VL3.

For all antibodies, washing away free antibody which could potentially inhibit binding by blocking binding sites on the virus-coated plate had no effect on the results, except at very high concentrations of Mab124-40 antibody, where multivalent binding to cells could be the cause.

In the next study, growth inhibition of C6VL/1 cells by antibodies specific for cell surface determinants was investigated. C6VL/1 cells were washed and shed free of virus as described above. Cells were plated at a low density (1.5×10$^4$cells/ml) in RPMI/10% FCS containing diluting amounts of antibody over the saturating range. After 60 hr of culture triplicate cultures were assessed for cell number using a colorimetric assay. In brief 100 μl volumes of MTT (3-[4,5-dimethylthiazol-2-yl]-2,5-diphenyl tetrazolium bromide) at 5 mg/ml were added to 100 μl volume of cells and after 4 hr the colored precipitate was dissolved using 0.04N HCl in isopropanol. Spectrophotometric readings were made on a microelisa reader using a test wavelength of 540 nm and a reference wavelength of 630 nm. C6VL/1 cells were tested for growth in the presence of GK1.5 (L3T4), B22-249 (H-2D$^b$) and Mab124-40 (clonotypic T-cell receptor).

The results showed that proliferation was inhibited in the presence of supersaturating concentrations of Mab1-24-40. The first dilution of antibody which did not inhibit C6VL/1 growth was the point at which antibody-induced agglutination of cells occurs, indicating that antibody and antigen are roughly in a zone of equivalence. In these experiments, B22-249 was not inhibitory, and GK1.5 inhibited very weakly. Anti-Thy-1.2 antibodies also inhibited growing of C6VL/1 cells, as has been reported previously for other T-cell lymphomas.

The above results demonstrate that one can inhibit binding of viruses to a cell having a receptor specific for a binding site on a protein of a retrovirus by binding to the CSMR or a protein adjacent to the CSMR. Furthermore, the clonotypic antibody to the T-cell CSMR specific for the retroviral antigen inhibits lymphoma proliferation in vitro at concentrations of antibody which are sufficient to inhibit RadLV/C6VL virus binding to the cells.

The above results support the use of specific binding members which specifically bind to cell surface membrane receptors involved with activation of cells in the resting phase to the cell division cycle, which receptors also bind to binding sites on retroviral proteins. Thus, by isolating all or a portion of the cell surface membrane receptor, one can prepare a wide variety of compounds which can be used in the diagnosis and therapy of retroviral-initiated tumors.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of tumor cells in a warm-blooded animal host, said method comprising:
    combining a physiological sample suspected of containing a cell surface membrane receptor (CSMR) with a compound capable of binding to said CSMR, where said CSMR is characterized by: (1) being involved in the activation of cells from the resting phase to the cell division cycle; and (2) capable of specifically binding to a binding site of a transforming retrovirus; and
    determining the level of complex formation between said compound and said CSMR as compared to a predetermined value, as indicative of the presence of tumor cells.

2. A method according to claim 1, wherein said cell is a lymphocyte.

3. A method according to claim 2, wherein said compound binds to the variable region of the recognition receptor for said lymphocyte.

4. A method according to claim 3, wherein said recognition receptor is an α, β-heterodimer of a T-cell.

5. A method according to claim 3, wherein said recognition receptor is an immunoglobulin.

6. A method for detecting lymphoma or leukemia in a mammalian host, which comprises:
    combining a physiological sample from said host containing lymphocytic cell surface membrane receptors, wherein said receptors are characterized by: (1) being the recognition receptor for the lymphocyte; and (2) specifically binding to a slow transforming retrovirus antigen binding site, with a monoclonal antibody specific for the variable region of said recognition receptor, under conditions permitting complex formation between said receptor and said monoclonal antibody; and
    determining whether the level of complex formation is elevated as compared to a predetermined value, where said elevation is indicative of abnormal cellular proliferation.

7. A method according to claim 6, wherein said sample is blood or blood fraction.

8. A method according to claim 7, wherein said sample is lymph node or other lymphoid tissue.

9. A method according to claim 7, wherein said mammalian host is human.

10. A method according to claim 6, wherein said lymphoma or leukemia is a T-cell lymphoma or leukemia and said recognition receptor is the $\alpha$, $\beta$-heterodimer.

11. A method according to claim 6, wherein said lymphoma or leukemia is B-cell lymphoma or leukemia and said recognition receptor is an immunoglobulin.

12. A method for treating a host suspected of having a tumor caused by a transforming retrovirus, said method comprising:

administering to said host a growth retarding amount of a compound which specifically binds to a cell surface membrane receptor of said tumor cell, wherein said receptor is characterized by: (1) being involved in the activation of a cell from the resting phase to the cell division cycle; and (2) specifically binding to an antigen of said retrovirus;

whereby the proliferation of said cells having said cell surface membrane receptor is retarded.

* * * * *